US011213270B2

(12) United States Patent
Krimsky (10) Patent No.: US 11,213,270 B2
(45) Date of Patent: *Jan. 4, 2022

(54) FISSURAL ASSESSMENT AND SURGICAL AND INTERVENTIONAL PLANNING

(71) Applicant: Covidien LP, Mansfield, MA (US)

(72) Inventor: William S. Krimsky, Forest Hill, MD (US)

(73) Assignee: Covidien LP, Mansfield, MA (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/733,309

(22) Filed: Jan. 3, 2020

(65) Prior Publication Data
US 2020/0163719 A1    May 28, 2020

Related U.S. Application Data

(63) Continuation of application No. 15/700,329, filed on Sep. 11, 2017, now Pat. No. 10,542,953.

(Continued)

(51) Int. Cl.
*A61B 6/00* (2006.01)
*A61B 34/10* (2016.01)
(Continued)

(52) U.S. Cl.
CPC ............ *A61B 6/5217* (2013.01); *A61B 6/032* (2013.01); *A61B 6/50* (2013.01); *A61B 6/5205* (2013.01);
(Continued)

(58) Field of Classification Search
CPC ......... A61B 6/032; A61B 6/50; A61B 6/5205; A61B 6/5217; A61B 17/00234;
(Continued)

(56) References Cited

U.S. PATENT DOCUMENTS 6,188,355 B1    2/2001  Gilboa
9,044,254 B2    6/2015  Ladtkow et al.
(Continued)

FOREIGN PATENT DOCUMENTS

WO    0010456 A1    3/2000
WO    0167035 A1    9/2001
(Continued)

OTHER PUBLICATIONS

European Search Report for Application No. 17193200.7 dated Dec. 19, 2017 (13 pages).
(Continued)

*Primary Examiner* — Ping Y Hsieh
*Assistant Examiner* — Jose M Torres
(74) *Attorney, Agent, or Firm* — Carter, DeLuca & Farrell LLP (57) ABSTRACT

Provided are systems, devices, and methods of planning a medical procedure. An exemplary method includes receiving image data of a patient's chest, identifying the patient's lungs in the image data, determining locations of fissures of the patient's lungs in the image data, generating a three-dimensional (3D) model of the patient's lungs based on the image data, the 3D model showing the fissures of the patient's lungs, displaying a view of the 3D model including the fissures of the patient's lungs for viewing by a clinician, receiving input from the clinician regarding a plan for the medical procedure, and displaying the plan for the medical procedure.

20 Claims, 5 Drawing Sheets

Related U.S. Application Data (60) Provisional application No. 62/400,208, filed on Sep. 27, 2016, provisional application No. 62/400,222, filed on Sep. 27, 2016.

(51) Int. Cl.

| *A61B 10/04* | (2006.01) |
|---|---|
| *G16H 30/40* | (2018.01) |
| *A61B 34/00* | (2016.01) |
| *G06T 19/00* | (2011.01) |
| *G16H 50/50* | (2018.01) |
| *G16H 40/63* | (2018.01) |
| *A61B 6/03* | (2006.01) |
| *G06T 7/00* | (2017.01) |
| *A61B 18/00* | (2006.01) |
| *A61B 90/00* | (2016.01) |
| *A61B 34/20* | (2016.01) |
| *A61B 17/00* | (2006.01) |
| *A61B 18/18* | (2006.01) |
| *A61B 10/00* | (2006.01) |

(52) U.S. Cl.
CPC .............. *A61B 10/04* (2013.01); *A61B 34/10* (2016.02); *A61B 34/25* (2016.02); *G06T 7/0012* (2013.01); *G06T 19/003* (2013.01); *G16H 30/40* (2018.01); *G16H 40/63* (2018.01); *G16H 50/50* (2018.01); *A61B 17/00234* (2013.01); *A61B 2010/0061* (2013.01); *A61B 2017/00809* (2013.01); *A61B 2018/00541* (2013.01); *A61B 2018/00577* (2013.01); *A61B 2018/1861* (2013.01); *A61B 2034/101* (2016.02); *A61B 2034/105* (2016.02); *A61B 2034/107* (2016.02); *A61B 2034/2051* (2016.02); *A61B 2034/2072* (2016.02); *A61B 2034/252* (2016.02); *A61B 2034/256* (2016.02); *A61B 2090/378* (2016.02); *G06T 2200/04* (2013.01); *G06T 2207/10081* (2013.01); *G06T 2207/30061* (2013.01)

(58) Field of Classification Search
CPC . A61B 34/10; A61B 34/25; A61B 2010/0061; A61B 2017/00809; A61B 2018/00577; A61B 2018/1861; A61B 2034/101; A61B 2034/105; A61B 2034/107; A61B 2034/252; A61B 2034/256; A61B 2034/2051; A61B 2034/2072; A61B 2090/378; G06T 7/0012; G06T 19/003; G06T 2200/04; G06T 2207/10081; G06T 2207/30061; G16H 30/40; G16H 40/63; G16H 50/50

See application file for complete search history.

(56) References Cited

U.S. PATENT DOCUMENTS

| 9,119,650 | B2 | 9/2015 | Brannan et al. |
|---|---|---|---|
| 9,247,922 | B2 | 2/2016 | Tsujita |
| 9,247,992 | B2 | 2/2016 | Ladtkow et al. |
| 9,247,993 | B2 | 2/2016 | Ladtkow et al. |
| 9,259,269 | B2 | 2/2016 | Ladtkow et al. |
| 9,370,398 | B2 | 6/2016 | Ladtkow et al. |
| 10,542,953 | B2 | 1/2020 | Krimsky |
| 2004/0252870 | A1* | 12/2004 | Reeves ................ G06T 7/0012 382/128 |
| 2005/0196024 | A1 | 9/2005 | Kuhnigk |
| 2007/0049861 | A1 | 3/2007 | Gundel |
| 2007/0092864 | A1 | 4/2007 | Reinhardt et al. |
| 2011/0085720 | A1 | 4/2011 | Averbuch |
| 2011/0255761 | A1* | 10/2011 | O'Dell ..................... G06T 7/41 382/131 |
| 2014/0046211 | A1 | 2/2014 | Ladtkow et al. |
| 2014/0105472 | A1 | 4/2014 | Yin et al. |
| 2014/0270441 | A1 | 9/2014 | Baker |
| 2014/0275952 | A1 | 9/2014 | Monroe et al. |
| 2014/0281961 | A1 | 9/2014 | Baker |
| 2014/0282216 | A1 | 9/2014 | Baker |
| 2015/0141809 | A1 | 5/2015 | Costello et al. |
| 2015/0238270 | A1 | 8/2015 | Raffy |
| 2015/0265257 | A1 | 9/2015 | Costello et al. |
| 2015/0294462 | A1* | 10/2015 | Yin ........................ G06T 19/20 382/128 |
| 2016/0000302 | A1 | 1/2016 | Brown et al. |
| 2016/0000303 | A1 | 1/2016 | Klein et al. |
| 2016/0000356 | A1 | 1/2016 | Brown et al. |
| 2016/0000414 | A1 | 1/2016 | Brown et al. |
| 2016/0000517 | A1 | 1/2016 | Kehat et al. |
| 2016/0000520 | A1 | 1/2016 | Lachmanovich et al. |
| 2016/0005168 | A1 | 1/2016 | Merlet |
| 2016/0005193 | A1 | 1/2016 | Markov et al. |
| 2016/0005224 | A1 | 1/2016 | Greenburg |
| 2016/0038248 | A1 | 2/2016 | Bharadwaj et al. |
| 2016/0058507 | A1 | 3/2016 | Dickhans |
| 2016/0174873 | A1 | 6/2016 | Greenburg et al. |
| 2016/0317224 | A1 | 11/2016 | Girotto et al. |
| 2016/0317225 | A1 | 11/2016 | Girotto et al. |
| 2016/0317229 | A1 | 11/2016 | Girotto et al. |
| 2016/0317230 | A1 | 11/2016 | Girotto et al. |
| 2016/0317231 | A1 | 11/2016 | Girotto et al. |

FOREIGN PATENT DOCUMENTS

| WO | 2014160341 A2 | 10/2014 |
|---|---|---|
| WO | 2015127355 A1 | 8/2015 |
| WO | 2016182943 A1 | 11/2016 |

OTHER PUBLICATIONS

European Search Report for Application No. 17193201.5 dated Jan. 3, 2018 (12 pages).

Lassen et al., Automatic Segmentation of the Pulmonary Lobes from Chest CT Scans based on Fissures, Vessels, and Bronchi, IEEE Transactions on Medical Imaging, vol. 32, No. 2,, Feb. 1, 2013, pp. 210-222.

Carson et al., Lung Cancer Staging: An Overview of the New Staging System and Implications for Radiographic Clinical Staging, Seminars in Roentgenology, vol. 46, No. 3, Mar. 9, 2011, pp. 187-193.

Wiemker et al., Unsupervised extraction of the pulmonary interlobar fissures from high resolution thoracic CT data; 2005, International Congress Series 1281, pp. 1121-1126.

Examination Report No. 1 for Australian Patent Application No. 2017232127, dated Apr. 19, 2018.

Office Action issued in corresponding Canadian Appl. No. 2,980,209 dated Jun. 28, 2019 (3 pages).

* cited by examiner

FISSURAL ASSESSMENT AND SURGICAL AND INTERVENTIONAL PLANNING

CROSS-REFERENCE TO RELATED APPLICATIONS

This application is a continuation of U.S. patent application Ser. No. 15/700,329, filed Sep. 11, 2017, entitled Fissural Assessment and Surgical and Interventional Planning, which claims the benefit of the filing date of provisional U.S. Patent Application Nos. 62/400,208 and 62/400,222, both filed Sep. 27, 2016.

INTRODUCTION

The present disclosure relates to the detection and assessment of fissures between lung lobes, and, more specifically, to systems, devices, and methods for using the detection and assessment of fissures between lung lobes in surgical and interventional planning. The disclosure further relates to the detection and assessment of an invasion by tumors or other aberrant structures in the pleural surfaces or other critical structures of the lungs, the pericardium, and/or the diaphragm, and, more specifically, to systems, devices, and methods for using the detection and assessment of an invasion of the pleura by aberrant structures in surgical and interventional planning.

BACKGROUND

Pulmonary disease may cause one or more portions of a patient's lungs may lose its ability to function normally and thus may need to be surgically resected. Surgical resection procedures may be very complex and would be greatly aided if the surgeon performing the procedure can visualize the way the diseased lung portions are shaped, and particularly how the fissures between the different portions of the lungs are developed or may have been deformed due to the disease.

Generally, a patient's lungs are divided into 5 lobes: an upper, middle, and lower lobe comprising the right lung, and an upper and lower lobe comprising the left lung. The lungs are surrounded by the pulmonary pleura. The pleura are composed of two serous membranes: the outer parietal pleura line the inner wall of the rib cage, and the inner visceral pleura directly line the surface of the lungs. The lung lobes are formed by recessions in the pleura, also known as fissures. The fissures are double folds of the pleura that section the lungs into the different lobes. Both the right and left lungs also have a central recession called the hilum at the root of the lung where airways, vascular, and lymphatic lumens pass into the lungs.

By viewing the patient's lungs prior to surgery, the clinicians and surgeons may visualize exactly how the patient's lungs are formed, the locations of the various lobes and fissures, where any potential incomplete fissures are located, the degree of incompleteness of any of the fissures, and potential vascular abnormalities that might be associated with this. However, it is very difficult to accurately visualize the fissures of the lungs by simply viewing computed tomography (CT) images of the patient's chest. As such, surgeons often start a surgery without prior knowledge of the degree of completeness of the fissures and the corresponding vascular anatomy. Complete fissures typically improve the ease with which a surgical resection can be performed, especially where the fissure constitutes one boundary of the resection—such as in a lobectomy. The fissures can also impute the potential for collateral airflow between segments and lobes with the attendant effects noted in patients with emphysema or other lung diseases. Further, when fissures are incomplete, identification of the vascular bundle subtending that area becomes more challenging and can also imply aberrancy with respect to vascular distributions. Thus, discovery of incomplete fissures at the time of surgical resection can be quite troublesome and render an otherwise uncomplicated surgery quite a bit more complicated as vascular structures need to be identified, etc., and therefore lengthening operative times. In procedures to treat other lung diseases, such as emphysema, advance knowledge of the degree of completeness of the fissures can also have a substantive impact on how those procedures are approached. Systems, devices, and methods for improving on the process of identifying and visualizing fissures of a patient's lungs are described below.

SUMMARY

Provided in accordance with the present disclosure is a method of planning a medical procedure. In an aspect of the present disclosure, the method includes receiving image data of a patient's chest, identifying the patient's lungs in the image data, determining locations of fissures of the patient's lungs in the image data, generating a three-dimensional (3D) model of the patient's lungs based on the image data, the 3D model showing the fissures of the patient's lungs, displaying a view of the 3D model including the fissures of the patient's lungs for viewing by a clinician, receiving input from the clinician regarding a plan for the medical procedure, and displaying the plan for the medical procedure.

In another aspect of the present disclosure, displaying the plan includes displaying a view of the 3D model showing areas of the patient's lungs to be treated.

In a further aspect of the present disclosure, the method further includes determining locations of lumens in the image data, and the displayed view of the 3D model further includes the locations of the lumens in the patient's lungs.

In yet a further aspect of the present disclosure, displaying the plan further includes displaying a view of the 3D model showing locations of lumens in the patient's lungs in the areas of the patient's lungs to be treated.

In another aspect of the present disclosure, the lumens in the patient's lungs include one or more of airway, vascular, and lymphatic lumens.

In a further aspect of the present disclosure, the locations of the fissures of the patient's lungs are determined based on the determined locations of lumens in the patient's lungs.

In yet a further aspect of the present disclosure, the method further includes determining a degree of completeness of the fissures of the patient's lungs, and determining a point where incompleteness of a fissure begins.

In a further aspect of the present disclosure, the method further includes adjusting the plan for the medical procedure based on the determined locations of fissures and lumens in the image data, and displaying the adjusted plan for the medical procedure.

In yet a further aspect of the present disclosure, the plan for the medical procedure is adjusted when it is determined that lumens in a first area of the patient's lungs are connected to lumens in a second area of the patient's lungs.

In still a further aspect of the present disclosure, the first and second areas of the patient's lungs are first and second lobes of the patient's lungs.

In another aspect of the present disclosure, the first and second areas of the patient's lungs are first and second portions of a single lobe of the patient's lungs.

In yet another aspect of the present disclosure, the method further includes treating the areas of the patient's lungs shown on the view of the 3D model.

Provided in accordance with the present disclosure is a system for planning a medical procedure. In an aspect of the present disclosure, the system includes a computing device configured to receive image data of a patient's chest, identify the patient's lungs in the image data, determine locations of fissures of the patient's lungs in the image data, and generate a three-dimensional (3D) model of the patient's lungs based on the image data, the 3D model showing the fissures of the patient's lungs. The system further includes a display device configured to display a plan for the medical procedure, the plan including a view of the 3D model showing the fissures of the patient's lungs, and a tool for performing a procedure on the patient's lungs based on the plan for the medical procedure.

In another aspect of the present disclosure, the view of the 3D model shows areas of the patient's lungs to be treated.

In a further aspect of the present disclosure, the computing device is further configured to determine locations of lumens in the image data, and the displayed view of the 3D model further shows the locations of the lumens in the patient's lungs in the areas of the patient's lungs to be treated.

In yet a further aspect of the present disclosure, the lumens in the patient's lungs include one or more of airway, vascular, and lymphatic lumens.

In another aspect of the present disclosure, the computing device is further configured to adjust the plan for the medical procedure based on the determined locations of fissures and lumens in the image data, and wherein the display is further configured to display the adjusted plan for the medical procedure.

In yet another aspect of the present disclosure, the plan for the medical procedure is adjusted when it is determined that lumens in a first area of the patient's lungs are connected to lumens in a second area of the patient's lungs.

Provided in accordance with the present disclosure is a non-transitory computer-readable storage medium storing instructions which, when executed by a computer, cause the computer to receive image data of a patient's chest, identify the patient's lungs in the image data, determine locations of fissures of the patient's lungs in the image data, generate a three-dimensional (3D) model of the patient's lungs based on the image data, the 3D model showing the fissures of the patient's lungs, cause a display device to display a view of the 3D model including the fissures of the patient's lungs for viewing by a clinician, receive input from the clinician regarding a plan for the medical procedure, and cause the display device to display the plan for the medical procedure.

In another aspect of the present disclosure, the instructions further configure the computer to determine locations of lumens in the image data, determine a degree of completeness of the fissures of the patient's lungs, determine a point where incompleteness of a fissure begins, and the displayed view of the 3D model further includes the locations of the lumens in the patient's lungs.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

This disclosure is directed to devices, systems, and methods for performing fissural assessment and surgical and interventional planning. More particularly, the disclosure relates to preoperative segmental and subsegmental delineation and extrapolation of a visual representation of a patient's lungs, including the fissures of the patient's lungs and/or tumors or other aberrant structures that may have invaded the pleural surfaces or other critical structures of the lungs, the pericardium, and/or the diaphragm. The delineation may be performed using one or more software applications executing on a computer. The application may, for example, generate a three-dimensional (3D) model or map of the patient's lungs based on radiographically obtained images data, such as CT image data, to use for the visual representation of the patient's lungs. The 3D model may show, among other things, the pleura and other structures of the patient's lungs. The image data may further be processed to identify one or more treatment targets, such as tumors or other aberrant structures, in the patient's lungs. The application may further determine whether one or more of the treatment targets have invaded the pleural surfaces or other critical structures of the lungs, the pericardium, and/or the diaphragm. For example, the application may identify the locations of lumens, such as airways, blood vessels, and/or lymphatic structures from the CT image data, and, based on the locations of the lumens, determine where lung fissures and located and a degree of completeness of the fissures, as well as determine the locations of the pleura, the pericardium, the diaphragm and/or treatment targets. The 3D model may then be viewed by a clinician and/or surgeon to plan a medical treatment procedure, such as a surgical or interventional procedure. The 3D model and/or treatment plan may further be stored for later viewing during the treatment procedure in an operating room or the like.

The 3D model of the patient's lungs may also be used to plan the treatment procedure, such as to mark areas intended to be treated, for example, by an ablation and/or resection procedure, as well as other areas of interest in the patient's lungs. By using CT image data collected while the patient's lungs are inflated, e.g. at breath-hold, and when the patient's lungs are deflated, the 3D model may be used to visualize the patient's lungs at different states of inflation. Further, the 3D model may also show the vasculature and airways inside the patient's lungs and how such vascular and airway lumens move during the breathing cycle. By visualizing the location of the vasculature and airways at different stages of the breathing cycle, the clinician may ensure that all the appropriate airways and vasculature are contained in the treatment plan. This is especially helpful to clinicians performing robotic and/or video-assisted thoracic surgery (VATS) which provides a much more limited field of view than traditional surgical methods.

Additionally, increasing the speed of the treatment procedure, given that extensive intraoperative searches to identify potentially aberrant anatomic structures, i.e. airways, vasculature, etc., may be very time consuming and could potentially eliminate certain patients from being considered for surgery who might benefit therefrom. By generating the 3D model, the application may further be able to create a predictive model with respect to several variables, including difficult lung geometries, portending difficult treatment procedures, and may identify normal and abnormal anatomic structures, all of which may assist the clinician during performance of the treatment procedure.

In accordance with embodiments of the present disclosure, it is contemplated that a predictive approach may be utilized. Such an approach may better enable a clinician to determine whether the planned procedure will have the desired outcome or will result in deleterious effects. In this manner, the clinician initially records patient data corresponding to the patient's vitals, such as pulmonary function (through a Pulmonary Function Tests, blood gas analysis, or the like), cardiac function (i.e., heart rate, or the like), respiration rate, oxygen saturation, and breathing effort and enters this information into a database. Additionally, identifying information such as age, gender, height, weight, race, national origin, or the like, disease type and planned procedure, in addition to the patient's medical history is recorded. Over time, a database may be built using the data obtained during each procedure. This database may be indexed such that clinicians may review data obtained from similar patients to better predict the outcome of the procedure.

In further embodiments, it is contemplated that images of the patient obtained by a suitable imaging modality may be correlated or indexed to patient data to enable a clinician to look up similarly situated patients. In this manner, the clinician may better predict the clinical consequences of the planned procedure, as will be described in further detail hereinbelow.

After performing a temporary or permanent procedure, the clinician observes the patient to determine the clinical consequences of the procedure. In this manner, the clinician may monitor the heart rate, respiration rate, oxygen saturation, breathing effort, or other vital signs indicative of whether the procedure has improved the patient's condition, maintained the patient's condition, or degraded the patient's condition. Using this information, the clinician determines whether the procedure produced the desired clinical effect. Some of these effects may be immediately apparent while others may require some time to materialize. In instances where the effects are not immediately apparent, once the patient is allowed to awaken from the procedure, a clinical assessment using both qualitative and quantitative measures can be undertaken. The clinician may record the clinical effects of the procedure in the database. In this manner, the location at which the procedure was undertaken is recorded and correlated to the location of the area of interest and the clinical record of the patient. It is further contemplated that the type of treatment being proposed, the volume of the treatment area including the amount of tissue being treated, the type of tissue being targeted, dynamic measures of integrated function (e.g., the six minute walk test), and qualitative metrics (e.g., St. Georges Respiratory Questionnaire) may be recorded and correlated to the patient data.

By recording the above described information, the clinical consequences of the procedure are made accessible by clinicians performing similar procedures in the future, and may be used to predict the clinical effect of similar procedures in the future. As can be appreciated, once the database is populated with a number of procedures and/or patients, a clinician will be able to predict or otherwise determine whether the planned procedure would produce the desired clinical effects. For example, a patient suffering from emphysema affecting a portion of the lungs located in the upper portion of the right lobe may be correlated to a similar patient having emphysema affecting a portion of the lungs located in the upper portion of the right lobe whose data has been entered into the database. In this manner, the clinician is able to predict whether the planned procedure would produce the desired clinical effects. Indeed, by predicting whether a patient would benefit from removal or isolation of a particular portion of the lung, the clinician is able to reduce the number or procedures required to treat the patient (i.e., eliminating or vastly reducing a trial and error approach), thereby reducing pain, recovery time, and expense. Further, this predictive model provides a basis to determine whether a patient's outcome meets the prediction or falls short and if it falls short the clinician may be able to identify one or more aggravating factors not previously contemplated and perform further procedures. The data of these procedures is recorded and used to further the database for future clinicians.

It is further contemplated that the above detailed predictive approach may be utilized in conjunction with tracking system 70 (FIG. 1) to facilitate navigation of tools 102, 104 to a location adjacent the area of interest and or tracking of tools 102, 104 as it is manipulated to treat the identified tissue.

Once the area of interest is identified, the patient is compared to information stored in the database pertaining to other patients using a suitable software application executed by the processor. The process of identifying the area of interest is similar to that described above, and thus, will not be detailed herein for purposes of brevity. The software application compares the current patient's characteristics and the location of the area of interest to the entries populating the database, and using a mathematical computation or other similar means, identifies a particular patient or set of patients to which the current patient substantially aligns. As can be appreciated, the software application may assign a percentage or other identifier (e.g., ranking, number of similar characteristics, or the like) to patients stored within the database, such that the current patient may be considered a 100% match, 95% match, or the like. It is further contemplated that the software application may rank or otherwise compile, in descending or ascending order, a list of identified patients. Using this information, the clinician may make an educated determination as to the likelihood that removing or isolating that particular portion of the vascular structure would produce the desired clinical effect. With this information available to the clinician during the planning phase, the clinician may make an informed decision to either temporarily perform the procedure using one or more of the procedures detailed above or permanently treat the tissue (i.e., isolate and/or remove the tissue or vascular structure) containing or serving the area of interest.

Finally, using the software application described above, the clinician observes the clinical effects similarly to that described above, and thereafter, records the clinical effects of the procedure and enters the information into the database. In embodiments, it is envisioned that the clinician records the clinical effects regardless of whether he chose to permanently or temporarily treat the portion of the lungs including the area of interest. This ensures that the database is continually updated such that further clinicians receive the most up to date and reliable information possible when planning future procedures.

Yet a further aspect of the present disclosure is a predictive outcome application. With all the procedures described herein, there will be follow-up CT imaging and most likely pulmonary function testing. These data, particularly the CT image data and particularly contrast enhanced CT imaging or PET/CT imaging, can be collected in an effort to identify the actual outcomes associated with the treatments described herein and at a minimum determine if follow-up procedures are necessary. By comparing actual outcomes to the treatment parameters better guidelines can be given to the clinicians. More importantly the planning software (described above) can rely on this data to adjust the expected treatment zone given a wide array of factors including size of alveolus or lung parencyma treated, size of blood vessels in the treatment area, location in the lung (e.g., which bifurcation), power and duration of ablation and others. As a result, over time the predictions in the planning software are refined to provide greater accuracy. It is also anticipated that the above described software could alert surgeons and proceduralists to aberrant distributions of the vasculature that would be valuable to know pre-procedurally. In this manner, the identified aberrant distributions could be used to alter operative or procedural planning.

The methods, systems, devices, and computer-readable media described herein are useful in various planning and/or navigation contexts for treatment procedures performed on the patient's lungs and surrounding tissue. For example, in an embodiment in which a clinician is performing treatment of an area of the patient's lungs, the methods and systems may provide the clinician with various views and estimations of the locations and completeness of the fissures of the patient's lungs, as well as the locations of the pleura and treatment targets that may invade the pleural surfaces or other critical structures of the lungs, the pericardium, and/or the diaphragm. Additionally, as will be described in further detail below, the methods and systems may provide the clinician with adjusted plans for the treatment of an area of the patient's lungs based on detected fusions between airways, blood vessels, and other lumens from different areas and/or invasions of the pleura of the patient's lungs. These and other aspects of the present disclosure are detailed herein below.

Methods for planning and performing treatment of an area of a patient's lungs may be implemented via an electromagnetic navigation (EMN) system. Generally, in an embodiment, the EMN system may be used in planning treatment of an area of the patient's lungs by identifying the locations and completeness of fissures of the patient's lungs and of invasions of the pleura of the patient's lungs, determining a pathway to a target location such as a surgical site, navigating a positioning assembly to the target location, and navigating a variety of tools to the target location. The EMN system may be configured to display various views of the patient's body, and of the aforementioned 3D model.

Figure 1:
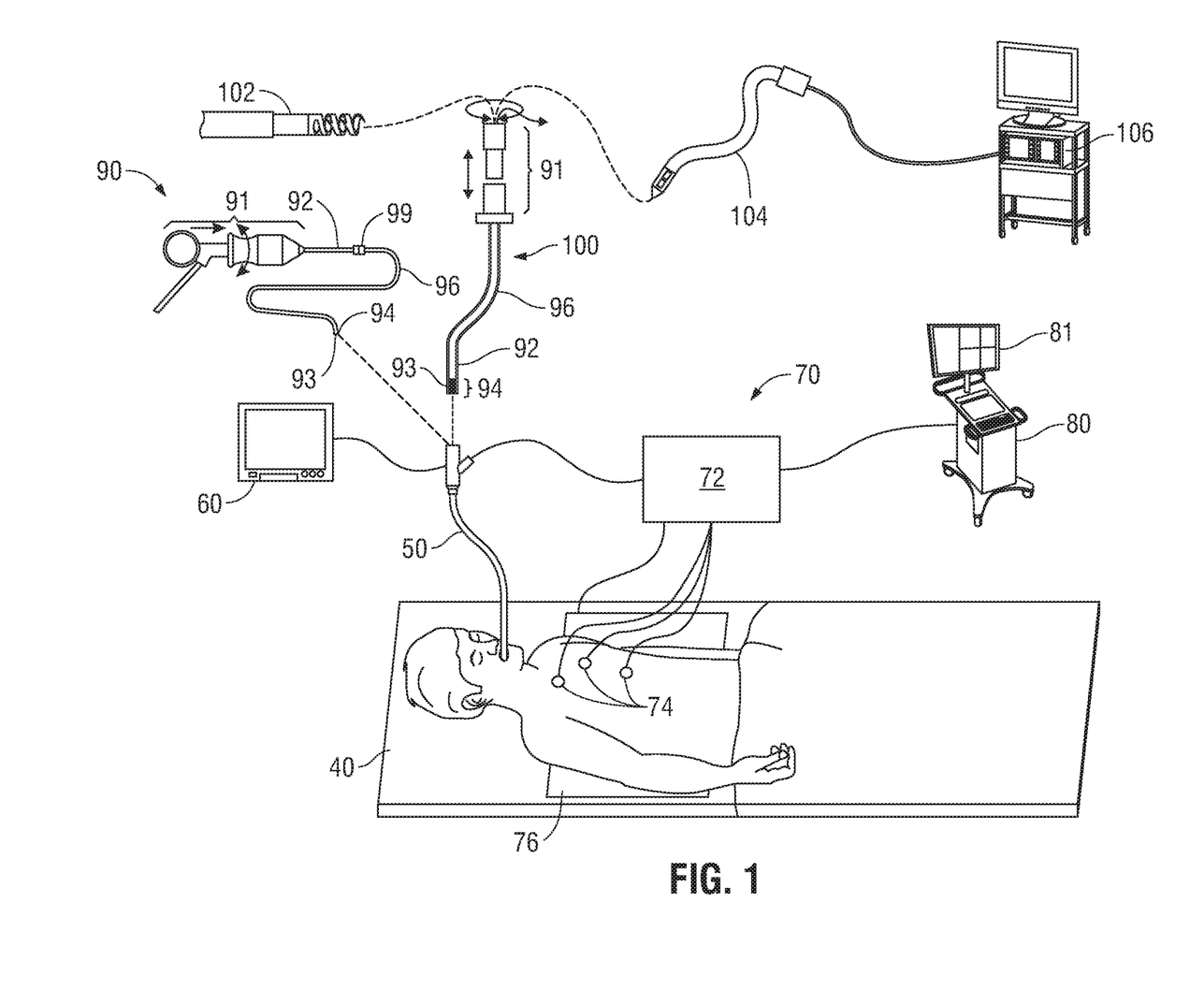
FIG. 1 is a schematic diagram of an endobronchial system for planning and performing treatment of an area of patient's lungs, according to an embodiment of the present disclosure.

With reference to FIG. 1, an EMN system 10 suitable for implementing methods for planning and performing treatment of an area of a patient's lungs is provided in accordance with the present disclosure. One such EMN system 10 is the ELECTROMAGNETIC NAVIGATION BRONCHOSCOPY® system currently sold by Covidien LP. As shown in FIG. 1, EMN system 10 is used to perform one or more treatment procedures on a patient supported on an operating table 40. In this regard, EMN system 10 generally includes a bronchoscope 50, monitoring equipment 60, an electromagnetic (EM) tracking system 70, and a computing device 80.

Bronchoscope 50 is configured for insertion through the patient's mouth and/or nose into the patient's airways. As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, for example, a video display, for displaying the video images received from the video imaging system of bronchoscope 50.

In an embodiment, bronchoscope 50 may operate in conjunction with a catheter guide assembly, two types of which are depicted in FIG. 1 (for example, catheter guide assemblies 90, 100). Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). Although configured differently, catheter guide assemblies 90, 100 share a number of common components. Specifically, each catheter guide assembly 90, 100 includes a handle 91, which is connected to an extended working channel (EWC) 96. In each assembly 90, 100, EWC 96 is sized for placement into the working channel of bronchoscope 50. In the operation of each assembly 90, 100, a locatable guide (LG) 92, including an EM sensor 94, is inserted into EWC 96 and locked into position such that EM sensor 94 extends a desired distance beyond the distal tip 93 of EWC 96. The location of EM sensor 94, and thus the distal end of EWC 96, within an EM field generated by EM field generator 76 can be derived by tracking module 72, and computing device 80. Catheter guide assemblies 90, 100 may have different operating mechanisms, but each includes handle 91 that can be manipulated by rotation and compression to steer distal tip 93 of LG 92 and EWC 96.

Catheter guide assembly 90 is currently marketed and sold by Covidien LP under the name SUPERDIMENSION® Procedure Kits. Catheter guide assembly 100 is currently sold by Covidien LP under the name EDGE™ Procedure Kits. Both kits include handle 91, EWC 96, and LG 92. For a more detailed description of catheter guide assemblies 90, 100, reference is made to commonly-owned U.S. Pat. No. 9,247,992, entitled "MICROWAVE ABLATION CATHETER AND METHOD OF UTILIZING THE SAME", filed on Mar. 15, 2013, by Ladtkow et al., the entire contents of which are hereby incorporated by reference.

LG 92 and EWC 96 are selectively lockable relative to one another via a locking mechanism 99. A six degrees-of-freedom EM tracking system 70, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dec. 14, 1998 by Gilboa, the entire contents of each of which is incorporated herein by reference, or any other suitable positioning measuring system, is utilized for performing navigation, although other configurations are also contemplated.

EM tracking system 70 may be configured for use with catheter guide assemblies 90, 100 to track the position of EM sensor 94 as it moves in conjunction with EWC 96 through the airways of the patient, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes application 81, where the data from sensors 74 are used to calculate a patient coordinate frame of reference.

Although EM sensor 94 is described above as being included in LG 92 it is also envisioned that EM sensor 94 may be embedded or incorporated within a biopsy tool 102 where biopsy tool 102 may alternatively be utilized for navigation without need of LG 92 or the necessary tool exchanges that use of LG 92 requires. Similarly, it is envisioned that EM sensor 94 may be embedded or incorporated within a microwave ablation tool 104, where microwave ablation tool 104 may alternatively be utilized for navigation without the need of LG 92 or the necessary tool exchanges that use of LG 92 requires.

According to an embodiment, biopsy tool 102 is configured to be insertable into catheter guide assemblies 90, 100 following navigation to a target location and removal of LG 92. Biopsy tool 102 may be used to collect one or more tissue sample from the target location, and in an embodiment, is further configured for use in conjunction with tracking system 70 to facilitate navigation of biopsy tool 102 to the target location, and tracking of a location of biopsy tool 102 as it is manipulated relative to the target location to obtain the tissue sample. Similarly, microwave ablation tool 104 is configured to be insertable into catheter guide assemblies 90, 100 following navigation to a target location and removal of LG 92. Microwave ablation tool 104 is configured to be operated with a microwave generator 106, and may include any of a variety of microwave ablation tools and/or catheters, examples of which are more fully described in U.S. Pat. Nos. 9,259,269; 9,247,993; 9,044,254; and 9,370,398, and U.S. Patent Application Publication No. 2014/0046211, all entitled "MICROWAVE ABLATION CATHETER AND METHOD OF USING THE SAME", filed on Mar. 15, 2013, by Ladtkow et al., the entire contents of each of which is incorporated herein by reference. Though shown as a biopsy tool and microwave ablation tool in FIG. 1, those of skill in the art will recognize that other tools including for example RF ablation tools, brachytherapy tools, and others may be similarly deployed and tracked without departing from the scope of the present disclosure.

For example, a variety of useable biopsy tools are described in U.S. Patent Publication No. 2015/0141809, entitled "DEVICES, SYSTEMS, AND METHODS FOR NAVIGATING A BIOPSY TOOL TO A TARGET LOCATION AND OBTAINING A TISSUE SAMPLE USING THE SAME", filed Sep. 17, 2014, by Costello et al., and U.S. Patent Publication No. 2015/0265257, entitled "DEVICES, SYSTEMS, AND METHODS FOR NAVIGATING A BIOPSY TOOL TO A TARGET LOCATION AND OBTAINING A TISSUE SAMPLE USING THE SAME", filed Dec. 9, 2014, by Costello et al., the contents of each of which are incorporated herein by reference and useable with the EMN system 10 as described herein.

Computing device 80 includes software and/or hardware, such as an EMN application 81, used to facilitate the various phases of an EMN procedure, including generating the 3D model, identification of a target location, planning a pathway to the target location, registration of the 3D model with the patient's actual airways, and navigation to the target location. For example, during procedure planning, computing device 80 utilizes computed tomographic (CT) scan, magnetic resonance imaging (MRI) scan, and/or positron emission tomography (PET) scan image data for generating and viewing the 3D model of the patient's airways, enables the identification of a target location on the 3D model (automatically, semi-automatically or manually), and allows for the determination and selection of a pathway through the patient's airways to the target location. While the CT scan image data may have gaps, omissions, and/or other imperfections included in the image data, the 3D model is a smooth representation of the patient's airways, with any such gaps, omissions, and/or imperfections in the CT scan image data filled in or corrected. The 3D model may be presented on a display monitor associated with computing device 80, or in any other suitable fashion. An example of the planning software described herein can be found in U.S. Patent Publication Nos. 2014/0281961, 2014/0270441, and 2014/0282216, filed by Baker et al. on Mar. 15, 2013, and entitled "PATHWAY PLANNING SYSTEM AND METHOD", the contents of all of which are incorporated herein by reference. Further examples of the planning software can be found in commonly assigned U.S. Patent Publication No. 2016/0000302, entitled "SYSTEM AND METHOD FOR NAVIGATING WITHIN THE LUNG", filed on Jun. 29, 2015, by Brown et al., the contents of which are incorporated herein by reference.

Using computing device 80, various views of the 3D model may be presented and may be manipulated by a clinician to facilitate identification of a target location and selection of a suitable pathway through the patient's airways to access the target location. As noted above, the target location may be a surgical site where the treatment is to be performed, and/or a portion of or entire lobe of the patient's lungs requiring treatment. The 3D model may include, among other things, a model airway tree corresponding to the actual airways of the patient's lungs, and showing the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleura and fissures of the lungs. Some or all of the aforementioned elements may be selectively displayed, such that the clinician may choose which elements should be displayed when viewing the 3D model. For example, EMN application 81 may be configured in various states to display the 3D model in a variety of view modes. For each view of the 3D model, the angle from which the 3D model is displayed may correspond to a view point. The view point may be fixed at a predefined location and/or orientation, or may be adjusted by the clinician operating computing device 80.

Computing device 80, via application 81, may further be configured to review the plan created by the clinician to determine if the plan accounts for all detected abnormalities in the lungs of the patient. For example, an abnormality may be detected where a lung fissure is determined to be partially incomplete or entirely absent. An abnormality may also be detected if airways, blood vessels, and/or lymphatic lumens from one lung lobe have fused with airways, blood vessels, or lymphatic lumens from another lung lobe, and thereby breached the division between the lung lobes. Computing device 80, via application 81, may further be configured to review the determined invasions of the pleura of the patient's lungs. For example, a pleural invasion may be determined where a detected location of a treatment target overlaps with a detected location of a pleural surface. A potential pleural invasion may also be determined where a detected location of a treatment target is within a predetermined distance from a detected location of a pleural surface. If computing device 80 determines that the plan created by the clinician does not account for all detected abnormalities and/or determined invasions of the pleural surfaces or other critical structures of the lungs, the pericardium, and/or the diaphragm, adjustments to the plan may be determined and presented to the clinician for review.

Following planning, a procedure may be undertaken in which EM sensor 94, in conjunction with tracking system 70, enables tracking of EM sensor 94 (and thus the distal end of EWC 96 or tool 102) as EM sensor 94 is advanced through the patient's airways following the pathway planned during the planning phase. As an initial step of the procedure, the 3D model is registered with the patient's actual airways. One potential method of registration involves navigating LG 92 into each lobe of the patient's lungs to at least the second bifurcation of the airways of that lobe. The position of LG 92 is tracked during this registration phase, and the 3D model is iteratively updated based on the tracked position of the locatable guide within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. Patent Publication No. 2016/0000356, entitled "REAL-TIME AUTOMATIC REGISTRATION FEEDBACK", filed on Jul. 2, 2015, by Brown et al., the contents of each of which are incorporated herein by reference. While the registration process focuses on aligning the patient's actual airways with the airways of the 3D model, registration also ensures that the position of vascular structures, pleura, and fissures of the lungs are accurately determined.

Figure 2:
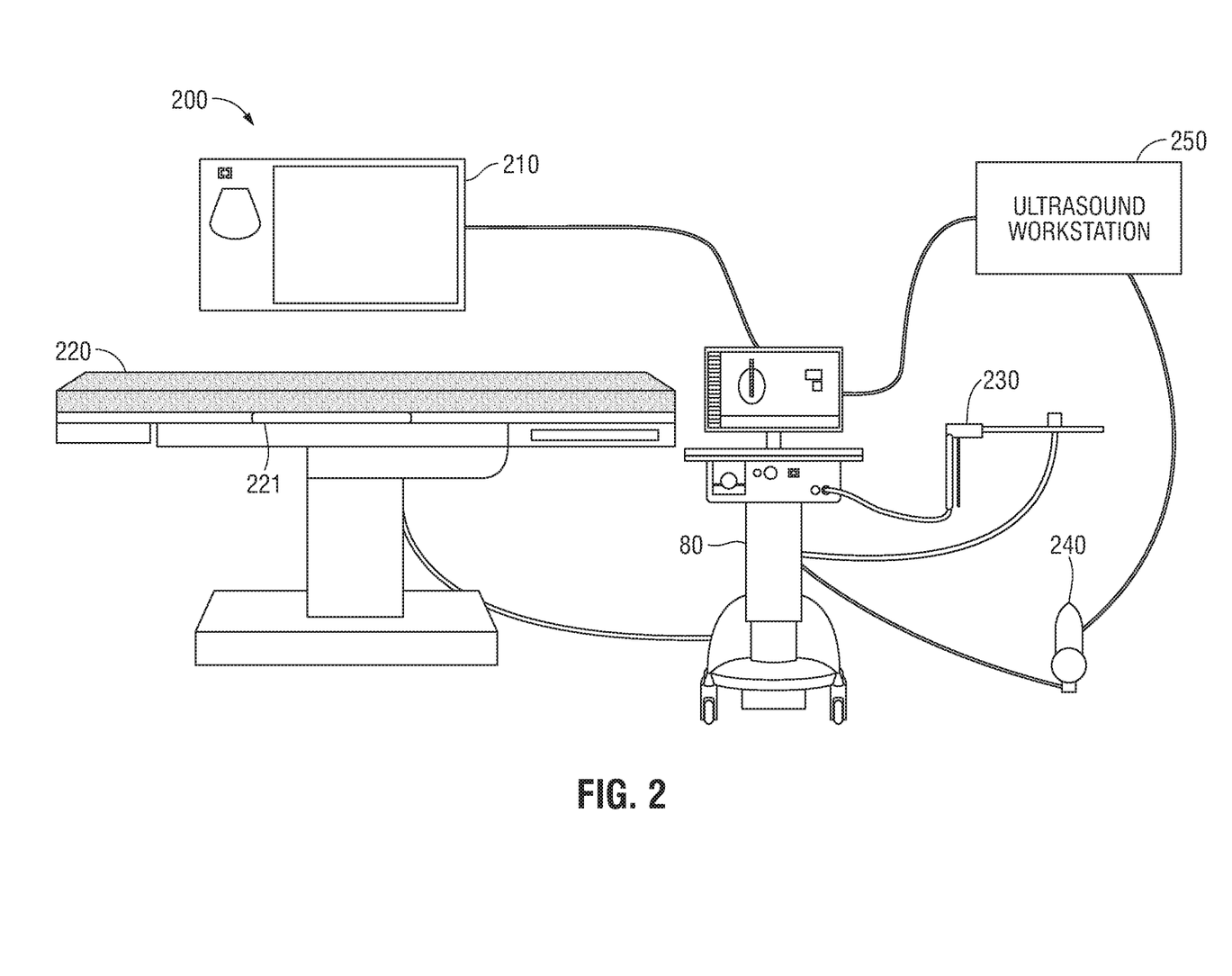
FIG. 2 is a schematic diagram of a percutaneous surgical planning and procedure system, according to an embodiment of the present disclosure.

With reference to FIG. 2, a percutaneous planning and procedure system 200 includes a computing device 80, a display 210, a table 220, a treatment tool 230, and an ultrasound sensor 240 connected to an ultrasound workstation 250. Similar to the computing device described above with reference to FIG. 1, computing device 80 may be, for example, a laptop computer, desktop computer, tablet computer, or other similar device. Computing device 80 may be configured to control an electrosurgical generator, a peristaltic pump, a power supply, and/or any other accessories and peripheral devices relating to, or forming part of, system 200. Display 210 is configured to output instructions, images, and messages relating to the performance of the treatment procedure. Table 220 may be, for example, an operating table or other table suitable for use during a treatment procedure, which includes an electromagnetic (EM) field generator 221. EM field generator 221 is used to generate an EM field during the treatment procedure and forms part of an EM tracking system that is used to track the positions of surgical instruments within the body of a patient. EM field generator 221 may include various components, such as a specially designed pad to be placed under, or integrated into, an operating table or patient bed. An example of such an EM tracking system is the AURORA™ system sold by Northern Digital Inc. Treatment tool 230 is a surgical instrument for percutaneously accessing and treating a target location. For example, treatment tool 230 may be an ablation probe having a microwave ablation antenna that is used to ablate tissue. While the present disclosure describes the use of system 200 in a surgical environment, it is also envisioned that some or all of the components of system 200 may be used in alternative settings, for example, an imaging laboratory and/or an office setting.

In addition to the EM tracking system, the surgical instruments may also be visualized by using ultrasound imaging. Ultrasound sensor 240, such as an ultrasound wand, may be used to image the patient's body during the treatment procedure to visualize the location of the surgical instruments, such as treatment tool 230, inside the patient's body. Ultrasound sensor 240 may have an EM tracking sensor embedded within or attached to the ultrasound wand, for example, a clip-on sensor or a sticker sensor. As described further below, ultrasound sensor 240 may be positioned in relation to treatment tool 230 such that treatment tool 230 is at an angle to the ultrasound image plane, thereby enabling the clinician to visualize the spatial relationship of treatment tool 230 with the ultrasound image plane and with objects being imaged. Further, the EM tracking system may also track the location of ultrasound sensor 240. In some embodiments, one or more ultrasound sensors 240 may be placed inside the body of the patient. EM tracking system may then track the location of such ultrasound sensors 240 and treatment tool 230 inside the body of the patient. Ultrasound workstation 250 may be used to configure, operate, and view images captured by ultrasound sensor 240.

Various other surgical instruments or surgical tools, such as LigaSure™ devices, surgical staples, etc., may also be used during the performance of a treatment procedure. In embodiment where treatment tool 230 is an ablation probe, the ablation probe is used to ablate a lesion or tumor (hereinafter referred to as a "target") by using electromagnetic radiation or microwave energy to heat tissue in order to denature or kill cancerous cells. The construction and use of a system including such an ablation probe is more fully described in co-pending US Patent Publication No. 2016/0058507, entitled MICROWAVE ABLATION SYSTEM, filed on Aug. 26, 2014, by Dickhans, U.S. Pat. No. 9,247,992 by Ladtkow et al., described above, and U.S. Pat. No. 9,119,650, entitled MICROWAVE ENERGY-DELIVERY DEVICE AND SYSTEM, filed on Mar. 15, 2013, by Brannan et al., the contents of all of which is hereby incorporated by reference in its entirety.

The location of treatment tool 230 within the body of the patient may be tracked during the treatment procedure. An example method of tracking the location of treatment tool 230 is by using the EM tracking system, which tracks the location of treatment tool 230 by tracking sensors attached to or incorporated in treatment tool 230. Various types of sensors may be used, such as a printed sensor, the construction and use of which is more fully described in co-pending U.S. patent application Ser. No. 14/919,950, entitled "MEDICAL INSTRUMENT WITH SENSOR FOR USE IN A SYSTEM AND METHOD FOR ELECTROMAGNETIC NAVIGATION", filed Oct. 22, 2015, by Greenburg et al., the entire contents of which is incorporated herein by reference. A percutaneous treatment system similar to the above-described system 200 is further described in co-pending U.S. patent application Ser. Nos. 15/099,698, 15/099,730, 15/099,772, 15/099,820, and 15/099,665, all filed on Apr. 15, 2016, by Girotto et al., the entire contents of each of which is incorporated herein by reference.

Figure 3:
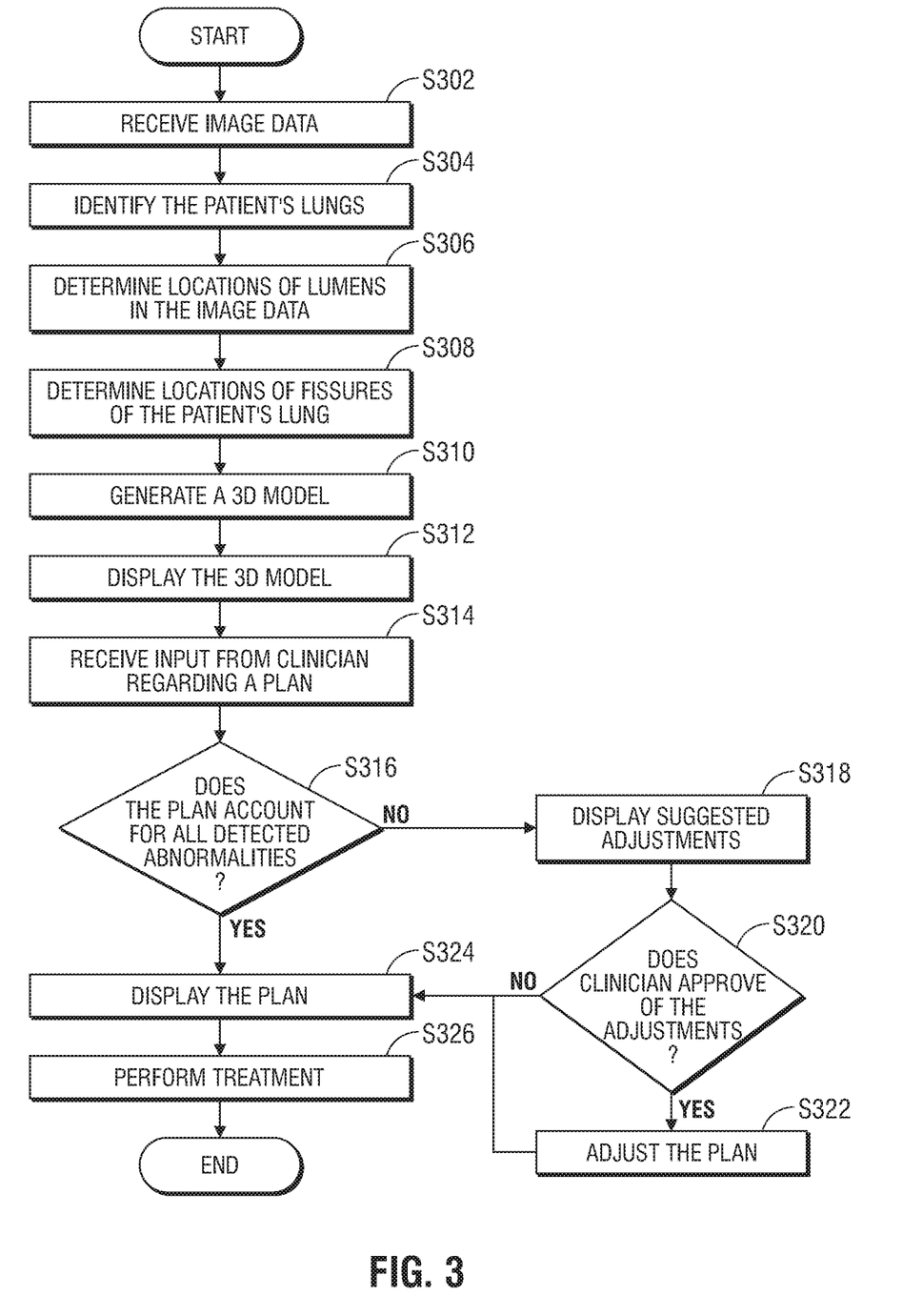
FIG. 3 shows a flowchart of an example method for planning and performing treatment of an area of a patient's lungs, according to an embodiment of the present disclosure.

Turning now to FIG. 3, there is shown a flowchart of an exemplary method of planning and performing treatment of an area of a patient's lungs, in accordance with an embodiment of the present disclosure. Starting at step S302, computing device 80 receives image data of the patient's lungs. The image data may be collected by one or more of various imaging modalities, including computed tomography (CT) scans, magnetic resonance imaging (MRI) scans, positron emission tomography (PET) scans, ultrasound scans, X-ray scans, and/or any other relevant imaging modality known to those skilled in the art. The image data may be received in, or converted to, a uniform data format, such as the digital imaging and communications in medicine (DICOM) standard.

Next, at step S304, application 81 processes the received image data to identify the patient's lungs in the image data. The image processing may include automatic and/or user-assisted image analysis to identify the patient's lungs in the image data. Various image processing methods may be used, including region growing techniques, as described in in co-pending U.S. Patent Publication No. 2016/0038248, entitled "TREATMENT PROCEDURE PLANNING SYSTEM AND METHOD", filed on Aug. 10, 2015, by Bharadwaj et al., and co-pending U.S. Patent Publication No. 2016/0005193, entitled "SYSTEM AND METHOD FOR SEGMENTATION OF LUNG", filed on Jun. 30, 2015, by Markov et al., the contents of both of which is incorporated herein by reference.

Thereafter, at step S306, application 81 determines the locations of lumens in the image data. The lumens may include airways of the patient's bronchial tree, arteries and veins of the patient's vascular tree, and/or lymphatic lumens and nodes of the patient's lymphatic tree. Thus, the lumens may be inside and/or outside of the patient's lungs. A healthy lung will typically have separate branches of each of the bronchial, vascular, and lymphatic trees in each lung lobe. However, as noted above, a diseased or malformed lobe may have lumens from the branches of one or more of these trees fused with lumens from the branches in an adjacent lobe. In such an instance, resecting of all or portions of both fused lung lobes may be necessary.

Next, at step S308, application 81 determines the locations of fissures of the patient's lungs. As noted above, fissures are folds in the pleura of the lungs which separate the lung lobes from each other. As with the identification of the lungs at step S304, the determination of the locations of the fissures of the lungs may include automatic and/or user-assisted image analysis, and may be based on the image data as well as various lung models to assist application 81 in identifying the locations of the fissures. For example, application 81 may process the image data based on the locations of the lumens determined at step S306 as well as the distribution of the corresponding parenchymal vasculature to determine the locations of the fissures of the lungs.

In addition to determining the locations of the fissures, application 81 may also determine a level or degree of completeness of the fissures. For example, where diseased or malformed lobes of the patient's lungs have fused together, the fissures may be incomplete or completely absent. Application 81 may determine the degree of completeness of the fissures based on the image data. For example, based on the locations of the lumens determined at step S306, application 81 may determine that lumens, i.e. airways, blood vessels, and/or lymphatic structures, of different lung lobes are interconnected, and thus indicate that at least a portion of a lung fissure is incomplete or entirely absent. Alternatively, application 81 may determine that lumens approaching an area where a fissure should be are "pruned," e.g., the lumens become vague and cannot clearly be identified, which may also indicate that at least a portion of a lung fissure is incomplete or entirely absent. In still another example, application 81 may determine that lumens adjacent to a lung fissure appear crisp and clear in the image data and can clearly be identified, which may indicate that at least a portion of the lung fissure is complete. In yet another example, application 81 may identify a thickness of the pleura and/or space between pleural boundaries, which may indicate that at least a portion of a lung fissure is complete. Based on one or more of these determinations, application 81 may identify the location where a lung fissure starts, and a level or degree of completeness of the lung fissure.

After steps S304-S308 have been completed, application 81 generates a three-dimensional (3D) model of the patient's lungs at step S310. The 3D model includes graphical representations of the patient's lungs, showing the locations of the lumens of the bronchial, vascular, and lymphatic trees, as well as the fissures. The model may further indicate where incomplete fissures exist and where lumens from adjacent lobes have fused together.

At step S312, the 3D model is displayed to the clinician, for example, by using a display device such as display 506 of FIG. 5, described below. The clinician may examine various views of the 3D model and determine which areas of the patient's lungs should be treated. The clinician may further examine the locations and level of completeness of the fissures of the patient's lungs to determine the complexity and scope of the procedure required to treat the diseased areas of the patient's lungs.

Thereafter, the clinician may generate a plan using computing device 80, for example, by using input device 510 of FIG. 5, described below. The clinician may select and/or mark various areas of the 3D model to identify those areas that require treatment. The areas may be one or more entire lobes of the patient's lungs, or one or more portions of a single lobe of the patient's lungs, or an identified tumor or lesion within the lungs. Application 81 may receive the input regarding the plan for the treatment procedure at step S314. As will be appreciated, consistent with the current iLogic™ planning system, this plan generation may occur prior to the generating of the 3D model, without departing from the scope of the present disclosure.

After receiving the plan, application 81 may examine the image data and/or the 3D model to determine, at step S316, if the plan accounts for all detected abnormalities in the patient's lungs. For example, application 81 may determine whether the plan accounts for incomplete fissures and/or fusing between bronchial, vascular, and/or lymphatic lumens from adjacent lung lobes. If application 81 determines that the plan does not account for all detected abnormalities in the patient's lungs, application 81 may display a notification to the clinician to warn the clinician of potential problems with the plan. Application 81 may also determine suggested adjustments to the plan to account for the detected abnormalities not accounted for by the plan and display the suggested adjustments at step S318. The clinician may review the suggested adjustments and may provide input to application 81 to approve or reject the suggested adjustments at step S320. If the clinician approves some or all of the suggested adjustments, application 81 may update and/or replace the plan with the adjusted plan at step S322.

Thereafter, at step S324, the plan and/or updated plan is displayed to the clinician, for example, by using display 506. The clinician may again review and approve the plan, and, at step S326, perform the treatment procedure by following the plan.

Figure 4:
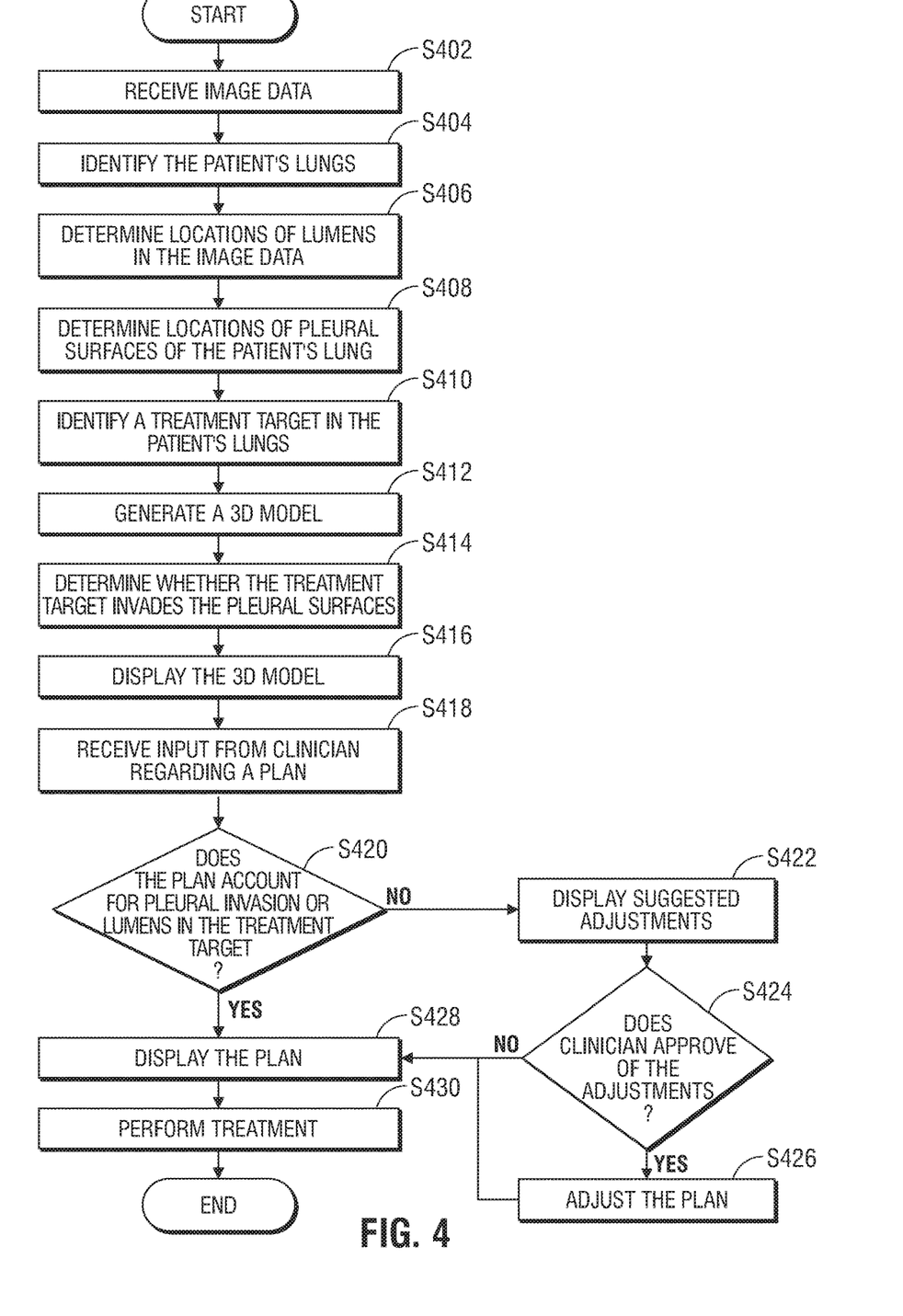
FIG. 4 shows a flowchart of another example method for planning and performing treatment of an area of a patient's lungs, according to an embodiment of the present disclosure.

Turning now to FIG. 4, there is shown a flowchart of another exemplary method of planning and performing treatment of an area of a patient's lungs, in accordance with an embodiment of the present disclosure. Starting at step S402, computing device 80 receives image data of the patient's lungs. The image data may be collected by one or more of various imaging modalities, including computed tomography (CT) scans, magnetic resonance imaging (MRI) scans, positron emission tomography (PET) scans, ultrasound scans, X-ray scans, and/or any other relevant imaging modality known to those skilled in the art. The image data may be received in, or converted to, a uniform data format, such as the digital imaging and communications in medicine (DICOM) standard.

Next, at step S404, application 81 processes the received image data to identify the patient's lungs in the image data. The image processing may include automatic and/or user-assisted image analysis to identify the patient's lungs in the image data. Various image processing methods may be used, including region growing techniques, as described above with reference to step S304 of FIG. 3.

Thereafter, at step S406, application 81 determines the locations of lumens in the image data. The lumens may include airways of the patient's bronchial tree, arteries and veins of the patient's vascular tree, and/or lymphatic lumens and nodes of the patient's lymphatic tree. Thus, the lumens may be inside and/or outside of the patient's lungs. A healthy lung will typically have separate branches of each of the bronchial, vascular, and lymphatic trees in each lung lobe. However, as noted above, a diseased or malformed lobe may have lumens from the branches of one or more of these trees fused with lumens from the branches in an adjacent lobe.

At step S408, application 81 determines the locations of pleural surfaces of the patient's lungs. In some embodiments, the locations of the pleural surfaces are determined based on the locations of the lumens determined at step S406. In other embodiments, the locations of the pleural surfaces are determined independently. In addition to the lumens and pleura, locations of various other structures, such as organs, bones, implantable devices, markers, and/or other aberrant structures may be determined.

Next, or concurrently with steps S404, S406, and/or S408, at step S410, application 81 identifies one or more treatments target in the patient's lungs. As with the identification of the lungs at step S404, the identification of the treatment targets in the lungs may include automatic and/or user-assisted image analysis, and may be based on the image data as well as various lung models to assist application 81 in identifying potential aberrant structures and/or tumors in the patient's lungs which may be identified as treatment targets. For example, application 81 may process the image data based on the locations of the lumens, pleura, and other structures determined at steps S406 and S408 to identify the treatment targets in the patient's lungs. Application 81 may further process the image data to detect distortion in the parenchyma surrounding the airways and/or small indentations in the lung fissures, which may be indicative of the presence of aberrant structures and/or deformities. In addition, application 81 may determine whether any lumens are located within the identified treatment targets. For example, various lumens, such as vascular lumens, may subtend or be contained within one or more treatment targets. Application 81 may further determine whether there are any aberrant lumens located within the patient's lungs, and particular, within or proximate the identified treatment targets. In another example where the treatment target is selected based on user-assisted image analysis, application 81 may selectively display the locations of lumens, pleural surfaces, organs, bones, implantable devices, markers, and/or other aberrant structures determined at steps S406 and/or S408. In an embodiment, the clinician may choose which structures to be shown, such as by highlighting or the like, thereby enabling application 81 to display only those structures which the clinician want to see in order to identify a treatment target.

After steps S404-S410 have been completed, application 81 generates a three-dimensional (3D) model of the patient's lungs at step S412. The 3D model includes graphical representations of the patient's lungs, showing the locations of the lumens of the bronchial, vascular, and lymphatic trees, as well as the pleura and the treatment target. The 3D model may further include the locations of organs, bones, implantable devices, markers, and/or other aberrant structures. At step S414, application 81 determines whether one or more of the treatment targets invade the pleural surfaces or other critical structures of the lungs, the pericardium, and/or the diaphragm. For example, application 81 may determine that a treatment target invades a pleural surface if an identified location of a treatment target overlaps with the determined location of a pleural surface. In addition, application 81 may determine a potential pleural invasion if an identified location of a treatment target is within a predetermined distance of the determined location of a pleural surface. Application 81 may further determine an assessment of the degree of pleural invasion by the one or more treatment targets. When a potential pleural invasion is detected, planning and/or staging for the treatment procedure may have to be adjusted to account for a more extensive surgical procedure, and therefore advance identification and notification of potential pleural invasions and aberrant lumens associated with the treatment target can greatly increase the efficiency and effectiveness of planning and performing the treatment procedure, and reduce unnecessary risk to the patient. Invasions of other critical structures of the lungs, the pericardium, and/or the diaphragm may likewise be detected.

Next, at step S416, the 3D model is displayed to the clinician, for example, by using a display device such as display 506 of computing device 80 (described below with reference to FIG. 5). Some or all of the structures included in the 3D model may be selectively displayed, that is, various views of the 3D model may be displayed and the clinician may choose which structures should be shown in each of the various views. The clinician may examine one or more of the various views of the 3D model and determine which areas of the patient's lungs should be treated. The clinician may further examine the locations and degree of pleural invasion and potential aberrant lumens of the patient's lungs to determine the complexity and scope of the procedure required to treat the identified treatment targets.

Thereafter, the clinician may generate a plan using computing device 80, for example, by using input device 510 (described below with reference to FIG. 5). The clinician may select and/or mark various areas of the 3D model to identify those areas that require treatment. The areas may include the one or more treatment targets identified at step S410. Application 81 may receive the input regarding the plan for the treatment procedure at step S418.

After receiving the plan, application 81 may reexamine the image data and/or the 3D model to determine, at step S420, if the plan accounts for all detected pleural invasions and potential aberrant lumens, as determined at steps S410 and S414. For example, application 81 may determine whether the plan accounts for each treatment target having a location that overlaps with the determined location of a pleural surface. If application 81 determines that the plan does not account for all pleural invasions or aberrant lumens, application 81 may display a notification to the clinician to warn the clinician of potential problems with the plan. Application 81 may also determine suggested adjustments to the plan to account for the detected pleural invasions or aberrant lumens not accounted for by the plan and display the suggested adjustments at step S422. The clinician may review the suggested adjustments and may provide input to application 81 to approve or reject the suggested adjustments at step S424. If the clinician approves some or all of the suggested adjustments, application 81 may update and/or replace the plan with the adjusted plan at step S426.

Thereafter, at step S428, the plan and/or updated plan is displayed to the clinician, for example, by using display 506. The clinician may again review and approve the plan, and, at step S430, perform the treatment procedure by following the plan. The displayed plan may include a view of the 3D model showing the areas of the patient's lungs to be treated and the locations of lumens and/or treatment targets in the areas of the patient's lungs to be treated.

Additional benefits of the above-described systems, devices, and methods are potential increases in the number of patients who are eligible for treatments, such as surgery, who may otherwise have been deemed too high-risk due to the potential length and extent of the treatment procedure required. Further, as described above, a predictive model may be developed, using data assembled over time as patients are treated and different anatomies are examined and based on patterns detected, to predict whether a particular fissure is likely to be intact or not, and a degree of incompleteness.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

As will be appreciated by those skilled in the art, the above-described methods may be performed using either and/or both of the endobronchial planning and navigation system 10 of FIG. 1 and the percutaneous planning and procedure system 200 of FIG. 2. For example, in planning a percutaneous treatment procedure, the clinician may take into account the locations of the pleura and pleural invasions when deciding on which access route to use to a particular treatment target.

Figure 5:
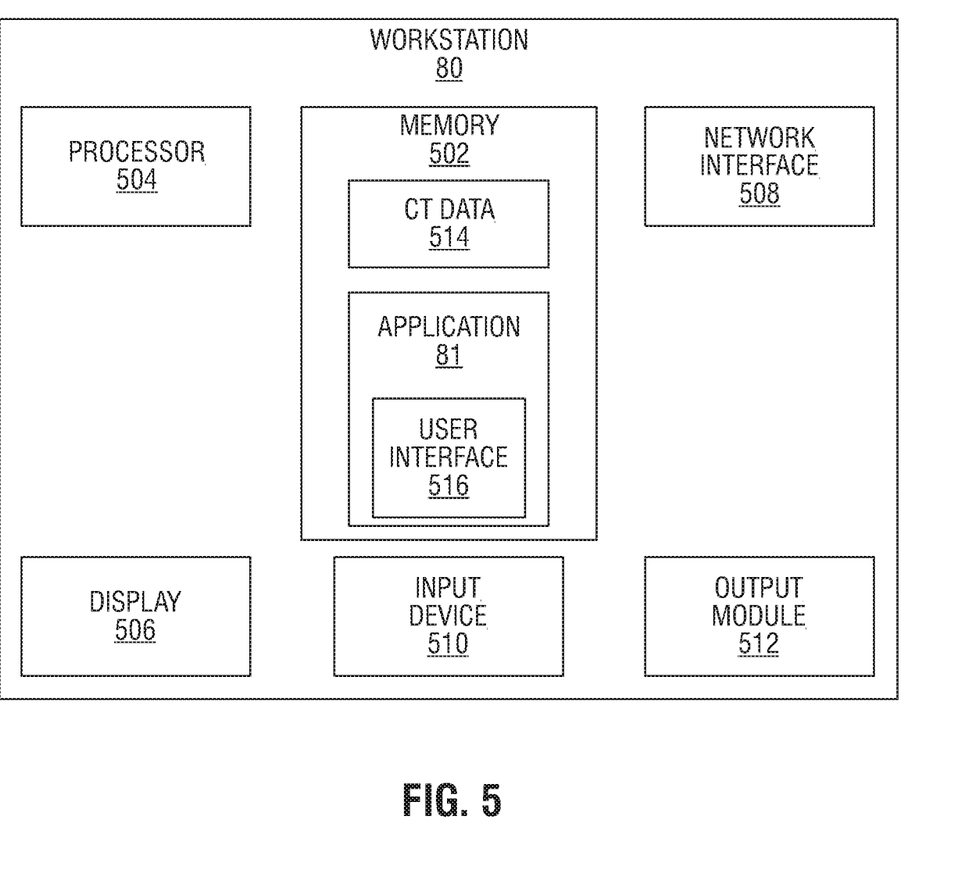
FIG. 5 is a diagram of an example computing device forming part of the systems of FIG. 1 or FIG. 2, according to an embodiment of the present disclosure.

Turning now to FIG. 5, there is shown a simplified block diagram of computing device 80. Computing device 80 may include a memory 502, a processor 504, a display 506, a network interface 508, an input device 510, and/or an output module 512. Memory 502 may store application 81 and/or image data 514. Application 81 may, when executed by processor 504, cause display 506 to present user interface 516. Application 81 may also provide the interface between the sensed position of EM sensor 94 and the image and planning data developed in the pathway planning phase.

Memory 502 may include any non-transitory computer-readable storage media for storing data and/or software that is executable by processor 504 and which controls the operation of computing device 80. In an embodiment, memory 502 may include one or more solid-state storage devices such as flash memory chips. Alternatively or in addition to the one or more solid-state storage devices, memory 502 may include one or more mass storage devices connected to the processor 504 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 504. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 508 may be configured to connect to a network such as a local area network (LAN) consisting of a wired network and/or a wireless network, a wide area network (WAN), a wireless mobile network, a Bluetooth network, and/or the internet. Input device 510 may be any device by means of which a user may interact with computing device 80, such as, for example, a mouse, keyboard, foot pedal, touch screen, and/or voice interface. Output module 512 may include any connectivity port or bus, such as, for example, parallel ports, serial ports, universal serial busses (USB), or any other similar connectivity port known to those skilled in the art.

Further aspects of image and data generation, management, and manipulation useable in either the planning or navigation phases of an EMN procedure are more fully described in commonly-owned U.S. Patent Publication No. 2016/0000414, entitled "METHODS FOR MARKING BIOPSY LOCATION", filed on Jun. 29, 2015, by Brown; U.S. Patent Publication No. 2016/0000517, entitled "INTELLIGENT DISPLAY", filed on Jun. 29, 2015, by Kehat et al.; U.S. Patent Publication No. 2016/0005224, entitled "UNIFIED COORDINATE SYSTEM FOR MULTIPLE CT SCANS OF PATIENT LUNGS", filed on Jul. 1, 2015, by Greenburg; U.S. Patent Publication No. 2016/0000303, entitled "ALIGNMENT CT", filed on Jul. 2, 2015, by Klein et al.; U.S. Patent Publication No. 2016/0005168, entitled "FLUOROSCOPIC POSE ESTIMATION", filed on May 29, 2015, by Merlet; and U.S. Patent Publication No. 2016/0000520, entitled "SYSTEM AND METHOD OF PROVIDING DISTANCE AND ORIENTATION FEEDBACK WHILE NAVIGATING IN 3D", filed on Jul. 2, 2015, by Lachmanovich et al., the contents of each of which are hereby incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of planning a lung procedure, the method comprising:

determining locations of lumens in an image of a patient's lungs;

determining locations of fissures of the patient's lungs in the image;

displaying a three-dimensional (3D) model of the patient's lungs based on the image;

displaying a plan for performing a lung procedure on the patient's lungs;

adjusting the plan for the lung procedure based on the determined locations of lumens and fissures in the image; and displaying the adjusted plan for the lung procedure.

2. The method according to claim 1, wherein displaying the plan includes displaying a view of the 3D model showing areas of the patient's lungs to be treated.

3. The method according to claim 2, wherein displaying the plan includes displaying a view of the 3D model showing the locations of the lumens in the patient's lungs in the areas of the patient's lungs to be treated.

4. The method according to claim 1, wherein the locations of the fissures are determined based on the determined locations of the lumens in the patient's lungs.

5. The method according to claim 1, wherein the 3D model shows the lumens in the patient's lungs and the fissures of the patient's lungs.

6. The method according to claim 1, further comprising:
determining a degree of completeness of the fissures of the patient's lungs; and
determining a point where incompleteness of a fissure begins.

7. The method according to claim 1, wherein the plan for the lung procedure is adjusted when it is determined that lumens in a first area of the patient's lungs are connected to lumens in a second area of the patient's lungs.

8. The method according to claim 7, wherein the first and second areas of the patient's lungs are first and second lobes of the patient's lungs.

9. The method according to claim 7, wherein the first and second areas of the patient's lungs are first and second portions of a single lobe of the patient's lungs.

10. A system for planning a lung procedure, the system including:
a display device configured to display a plan for performing a lung procedure on a patient's lungs; and
a computing device operably coupled to the display device and configured to:
determine locations of lumens in an image of the patient's lungs;
determine locations of fissures of the patient's lungs in the image;
generate a three-dimensional (3D) model of the patient's lungs based on the image; and
adjust the plan for the lung procedure based on the determined locations of fissures and lumens in the image.

11. The system according to claim 10, wherein the display device is configured to display the adjusted plan for the lung procedure.

12. The system according to claim 10, wherein the locations of the fissures are determined based on the determined locations of the lumens in the patient's lungs.

13. The system according to claim 10, wherein the 3D model shows the fissures of the patient's lungs and the lumens in the patient's lungs.

14. The system according to claim 10, wherein the plan includes a view of the 3D model showing the fissures of the patient's lungs.

15. The system according to claim 14, wherein the view of the 3D model shows areas of the patient's lungs to be treated.

16. The system according to claim 15, wherein the view of the 3D model shows the lumens in the patient's lungs in the areas of the patient's lungs to be treated.

17. A system for planning a lung procedure, the system including:
a display device configured to display a plan for performing a lung procedure on a patient's lungs; and
a computing device operably coupled to the display device and configured to:
determine locations of pleural surfaces of the patient's lungs in an image of the patient's lungs;
identify a treatment target in the patient's lungs;
generate a three-dimensional (3D) model of the patient's lungs based on the image;
determine whether the treatment target invades the pleural surfaces; and
adjust the plan for the lung procedure based on the determination that the treatment target invades the pleural surfaces.

18. The system according to claim 17, wherein the display device is configured to display the adjusted plan for the lung procedure.

19. The system according to claim 17, wherein the plan includes a view of the 3D model showing the pleural surfaces of the patient's lungs.

20. The system according to claim 17, wherein the 3D model shows the pleural surfaces of the patient's lungs and the treatment target.

* * * * *